United States Patent [19]
Nilsson et al.

[11] Patent Number: 5,888,815
[45] Date of Patent: Mar. 30, 1999

[54] CELL CULTIVATION METHOD AND MEDIUM

[75] Inventors: Helena Brink Nilsson, Sollentuna; Sarah Boork, Tidaholm, both of Sweden

[73] Assignee: Pharmacia & Upjohn Aktiebolag, Stockholm, Sweden

[21] Appl. No.: 632,443

[22] PCT Filed: Nov. 1, 1994

[86] PCT No.: PCT/SE94/01023

§ 371 Date: Apr. 15, 1996

§ 102(e) Date: Apr. 15, 1996

[87] PCT Pub. No.: WO95/12663

PCT Pub. Date: May 11, 1995

[30] Foreign Application Priority Data

Nov. 1, 1993 [SE] Sweden .................................. 9303601

[51] Int. Cl.$^6$ ............................. C12N 1/00; C13K 5/00; C13K 7/00; C07H 1/00
[52] U.S. Cl. ........................ 435/360; 435/358; 435/243; 536/123.13; 536/123.1
[58] Field of Search ..................... 435/358, 360, 435/243; 536/123.1, 123.13

[56] References Cited

U.S. PATENT DOCUMENTS

| | | | |
|---|---|---|---|
| 4,659,663 | 4/1987 | Wright | 435/172.2 |
| 4,786,599 | 11/1988 | Chessebeuf et al. | 435/240.31 |
| 5,422,250 | 6/1995 | Mignot et al. | 435/69.6 |

FOREIGN PATENT DOCUMENTS

| | | |
|---|---|---|
| 0 160 457 A1 | 4/1985 | European Pat. Off. . |
| 0 197 901 A1 | 4/1986 | European Pat. Off. . |
| 37 09 282 A1 | 10/1988 | Germany . |
| WO 91/09122 | 6/1991 | WIPO . |
| WO 92/05246 | 4/1992 | WIPO . |
| WO 92/16557 | 10/1992 | WIPO . |
| WO 94/11525 | 5/1994 | WIPO . |
| WO 94/19459 | 9/1994 | WIPO . |

OTHER PUBLICATIONS

Andersson et al., Isolation and characterization of human factor VIII: Molecular forms in commercial factor VIII concentrate, cryoprecipitate, and plasma, Medical Sciences, vol. 83 (1986), pp. 2979–2983.

Wood et al., Expression of active human factor VIII from recombinant DNA clones, Nature, vol. 312 (1984), pp. 330–337.

Rizzino et al., Defined Media and the Determination of Nutritional and Hormonal Requirements of Mammalian Cells in Culture, Nutrition Reviews, vol. 37, No. 12 (1979), pp. 369–378.

Barnes et al., Serum–free Cell Culture: a Unifying Approach, Cell, vol. 22 (1980), pp. 649–655.

Bödeker et al., A Screening Method to Develop Serum–Free Culture Media for Adherent Cell Lines, Develop. bio. Standard., vol. 60 (1985), pp. 93–100.

Gasser et al., Long–Term Multiplication of the Chinese Hamster Ovary (Cho) Cell Line in a Serum–Free Medium, In Vitro Cellular & Developmental Biology, vol. 21, No. 10 (1985), pp. 588–592.

Mendiaz et al., A Defined Medium for and the Effect of Insulin on the Growth, Amino Acid Transport, and Morphology of Chinese Hamster Ovary Cells . . . In Vitro Cellular & Developmental Biology, vol. 22, No. 2 (1986), pp. 66–74.

Meucci et al., Metal–catalyzed Oxidation of Human Serum Albumin: Conformational and Functional Changes, The Journal of Biological Chemistry, vol. 266, No. 8 (1991), pp. 4692–4699.

van der Pol et al., Effect of Reducing the Serum or Albumin. Chenciner et al., Enhancement of Gene Expression by Somatic Hybridization with Primary Cells: High–Level Synthesis of the Hepatitis B Surface Antigen in Monkey Vero Cells by Fusion with Primary Hepatocytes, Bio/Technology, vol. 8 (1990), pp. 858–862.

Morrison & Boyd, "Organic Chemistry" 3rd ed. 1973, see p. 1126.

Primary Examiner—Francisco Prats
Assistant Examiner—Deborah K. Ware
Attorney, Agent, or Firm—Pollock, Vande Sande & Amernick

[57] ABSTRACT

The invention relates to a method of cultivating mammalian cells expressing recombinant Factor VIII in a serum-free cell culture medium of the type that normally requires the presence of human serum albumin (HSA) and which is substantially free from fatty acids, fattyacid esters and lipids, but wherein HSA is replaced by at least one glucose or sucrose based polysaccharide having an average molecular weight of from about 10,000 to about 450,000. The invention also relates to such a serum-free cell culture medium.

13 Claims, 4 Drawing Sheets

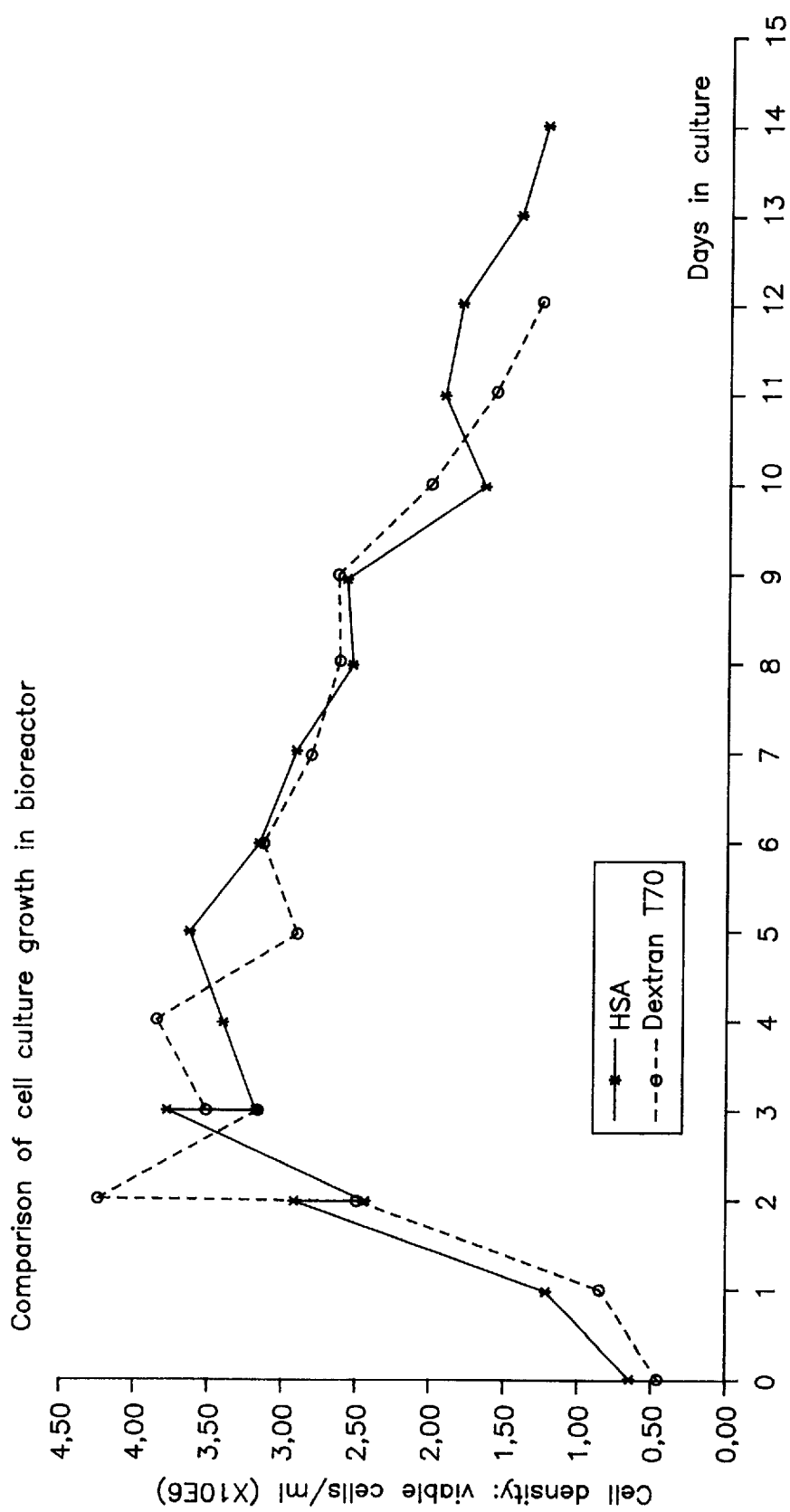

CELL CULTIVATION METHOD AND MEDIUM

BACKGROUND OF THE INVENTION

Factor VIII is a blood protein essential for the blood coagulation process. Lack of Factor VIII will reduce or prevent the coagulating ability of the blood, thereby causing a disease called hemophilia A. Patients suffering from this disease are treated with therapeutical preparations containing Factor VIII.

Factor VIII has conventionally been recovered from human blood plasma. Such Factor VIII concentrates contain several fragmented fully active Factor VIII forms (Andersson et al., Proc. Natl., Acad. Sci. U.S.A., Vol. 83, 2979–83, May 1986). The smallest active form has a molecular mass of 170 kDa and consists of two chains of 90 KDa and 80 KDa held together by a metal ion bridge, as disclosed in EP-A-197 901.

Factor VIII can, however, now also be produced as a recombinant protein expressed in mammalian cells, as described, for example, in J. Gitschier et al., Nature 312, 330–37, 1984 and EP-A-160 457. A truncated recombinant Factor VIII product which corresponds to the 170 kDa plasma Factor VIII is disclosed in WO 91/09122.

Media used for the cultivation of mammalian cells include a variety of nutrients and growth factors, many of which are traditionally supplied by serum. Serum is usually derived from either foetal calf, newborn calf or horse and added to the medium in concentrations from 0.5 to 20 % v/v. In addition to supplying growth enhancing components, serum also functions as a carrier/buffer/chelator for labile or water insoluble molecules, toxin neutraliser, protease inhibitor, cell attachment enhancer and as a protective agent in agitated suspension cultures.

The use of serum in cell culture media, however, has several disadvantages. It is comparatively expensive, it is not a defined component, and different lots of serum may vary in the concentration of compounds present and thus result in unpredictable culture growth and productivity. Serum may also be the source of contaminants such as mycoplasma, bacteriophages, virus and toxins. Additionally, the protein in serum may complicate the purification of cell products from cell culture media.

In efforts to overcome the disadvantages of serum containing medium, serum-free media have been developed in which serum is substituted with better defined or more characterised components. Due to the complexity of serum and the different growth requirements of cells, this has resulted in a variety of different media compositions. (For reviews it may be referred to Rizzino et al., Nutrition Reviews 37: 369–378 (1979); Barnes and Sato, Cell 22: 649–655 (1980); and Bodeker et al., Develop. Biol. Standard. 60: 93–100 (1985)). In most such serum-free media the serum is substituted by "cocktails" of trace elements, lipids, hormones, growth factors and purified proteins, for example serum albumin, and are therefore often only partially defined.

Media for the serum-free culture of Chinese hamster ovary (CHO) cells have been reported by Gasser et al., In-vitro Cellular Developmental Biology 21: 588–592 (1985), and Mendiaz et al., In-vitro Cellular Developmental Biology 22: 66–74 (1986). These media compositions, however, contain non-defined components derived from either human or animal source.

Albumin is considered a multifunctional transport protein for a broad spectrum of ligands including inorganic cations, organic anions, amino acids and hydrophobic molecules such as fatty acids (Meucci et al., Journal of Biological Chemistry 266: No. 8, 4692–4699 (1991). Due to the nature of human serum albumin (HSA), it is an important component in serum-free media used for the culture of cells expressing recombinant Factor VIII both in the context of cell growth and production. It is envisaged that it also acts as a stabiliser/protection factor for example against proteases and shear forces (van der Pol and Tramper, Effect of reducing the serum or albumin concentrations on the shear sensitivity of two hybridoma cell lines in sparged cultures. ESACT 11th Symposium, 1991).

The supplementation of cell culture media with HSA, however, potentially has similar disadvantages to the use of serum in media. Thus, it is expensive and periodically scarce, and HSA from different suppliers and even different lots may vary in the concentration of compounds present and therefore result in unpredictable culture growth and productivity. Serum albumin may also be the source of unknown contaminants and virus. Consequently, the replacement of HSA in the serum-free cell culture media used for the recombinant Factor VIII cell culture process by a non-human or non-animal derived substituent would be highly desirable.

WO 92/05246 generally discloses a serum-free mammalian cell culture medium for inter alia cells transformed to produce recombinant products, which medium comprises a synthetic basal medium, hydrolyzed yeast, albumin or dextran (specifically having a molecular weight of 500,000), insulin, transferrin or a transferrin substitute, and a fatty acid component.

EP-A-0441695 discloses a process for the preparation of Factor VIII or an analogue thereof in a cell culture medium containing a derivative of a polycationic or polyanionic polymer, such as dextran sulfate.

US-A-4,786,599 discloses a serum-free cell culture medium containing a mixture of fatty acids and albumin or dextran.

DE-A-3709282 discloses a lipid additive for cell culture media, which additive consists of lipids covalently bound to a water-soluble polymer such as starch, agarose, dextran or proteins.

SUMMARY OF THE INVENTION

The object of the present invention is to provide for the culture of recombinant Factor VIII, hereinafter for brevity referred to as "rVIII", in a serum-free medium that does not contain human serum albumin (HSA), and more particularly to replace HSA in a serum-free medium formulation used for the cultivation of mammalian cells expressing rVIII with a non-human or -animal derived component(s), without causing any diverse effects on cell growth characteristics or the production of rVIII.

In accordance with the present invention it has been found that HSA may be replaced by particular polysaccharide components to be defined below in the serum-free medium formulation used for the rVIII cell culture process. The resulting medium, which thus contains no human or animal derived products, permits the cell-line expressing the rVIII gene to be thawed directly into the medium and subsequently cultivated without any noticable effects to cell growth characteristics. Further, the medium will support "normal" cell growth in terms of viability, growth rate and morphology over extended culture periods, and it will also enable the cultivation of the rVIII-producing cell-line in a stirred tank bioreactor.

The present invention thus provides a method of cultivating mammalian cells expressing rVIII in a serum-free cell culture medium of the type that normally requires the presence of HSA and which is substantially free from fatty acids, fatty acid esters and lipids, which method is characterized in that HSA is replaced by at least one glucose or sucrose based polysaccharide having an average molecular weight of from about 10,000 to about 450,000, preferably from about 40,000 to about 400,000. The present invention also provides such a serum-free cell culture medium.

The term "recombinant Factor VIII" (or "rVIII") is to be understood in a broad sense and is meant to include any active form of recombinantly produced Factor VIII, including truncated forms.

The glucose or sucrose based polysaccharides include dextrans, such as partially hydrolyzed native dextran, and Ficoll, which is a trade name for a copolymer of sucrose and epichlorohydrin. Suitable commercially available dextran fractions are those having an average molecular weight of about 40,000 and 70,000, respectively.

The cell line is preferably a CHO cell line, and the preferred cell culture technique is suspension cell culture.

More specifically the method of the invention may be performed as follows.

A CHO cell line containing the rVIII gene is cultured as a suspension cell by conventional techniques in a serum-free medium which normally contains HSA but where HSA has been replaced by a polysaccharide as defined above. The serum-free medium may be based on a complete medium, such as CHO—S—SFM (GIBCO BRL), or a nutrient basal medium supplemented by a number of components. Such a supplemented basal medium may be prepared by adding components to the nutrient synthetic basal medium in accordance with standard procedures for preparing cell culture media.

The nutrient medium chosen for culturing the host cell line is not critical to the present invention, and may be one of, or a combination of those known to be suitable for the selected host cell line. Illustrative of such media are Dulbecco's Modified Eagle Medium, Eagle's Minimum Essential Medium, Ham's Medium F-12 and RPMI-1640 Medium.

Likewise, the factors added to the medium are not critical to the present invention and may be combinations of those known to the art which are suitable for the selected cell line, such as insulin, transferrin, ferric citrate, ascorbic acid, ethanolamine, glutamine, sodium selenite, etc. The amounts of such factors added to the nutrient medium are conventional to the art.

The pH of the medium is preferably from about pH 6.8 to 7.5, and the osmolality is preferably in the range from about 280 to 400 milliosmoles.

The polysaccharide component or components used as a supplement in replacement to HSA may be such commercially available, for example Dextran T fractions, such as T40 ($M_w$ 40,000) and T70 ($M_w$ 70,000), and Ficoll 70 ($M_w$ 70,000) or Ficoll 400 ($M_w$ 400,000), or the corresponding pharmaceutical grade products, for example from Pharmacia Biotech AB, Sweden. The supplement is conveniently added to the serum-free culture medium from a sterilized standard stock solution prepared from the polysaccharide component (s) and in an amount capable of maintaining the viability of the cells, the normal growth rate of the cells, and enabling the production of rVIII. Preferably, this amount is in the range of 0.05 to 5 grams per liter.

BRIEF DESCRIPTION OF THE DRAWINGS

The following non-limiting examples illustrate the invention, reference being made to the accompanying drawings, wherein

FIG. 4 is a diagram showing a comparison of cell culture growth in a bioreactor (cell density vs time) for a serum-free culture medium supplemented with HSA and dextran $M_w$ 70,000, respectively.

DETAILED DESCRIPTION OF THE INVENTION

EXAMPLE 1

Cell culture

Figure 1:
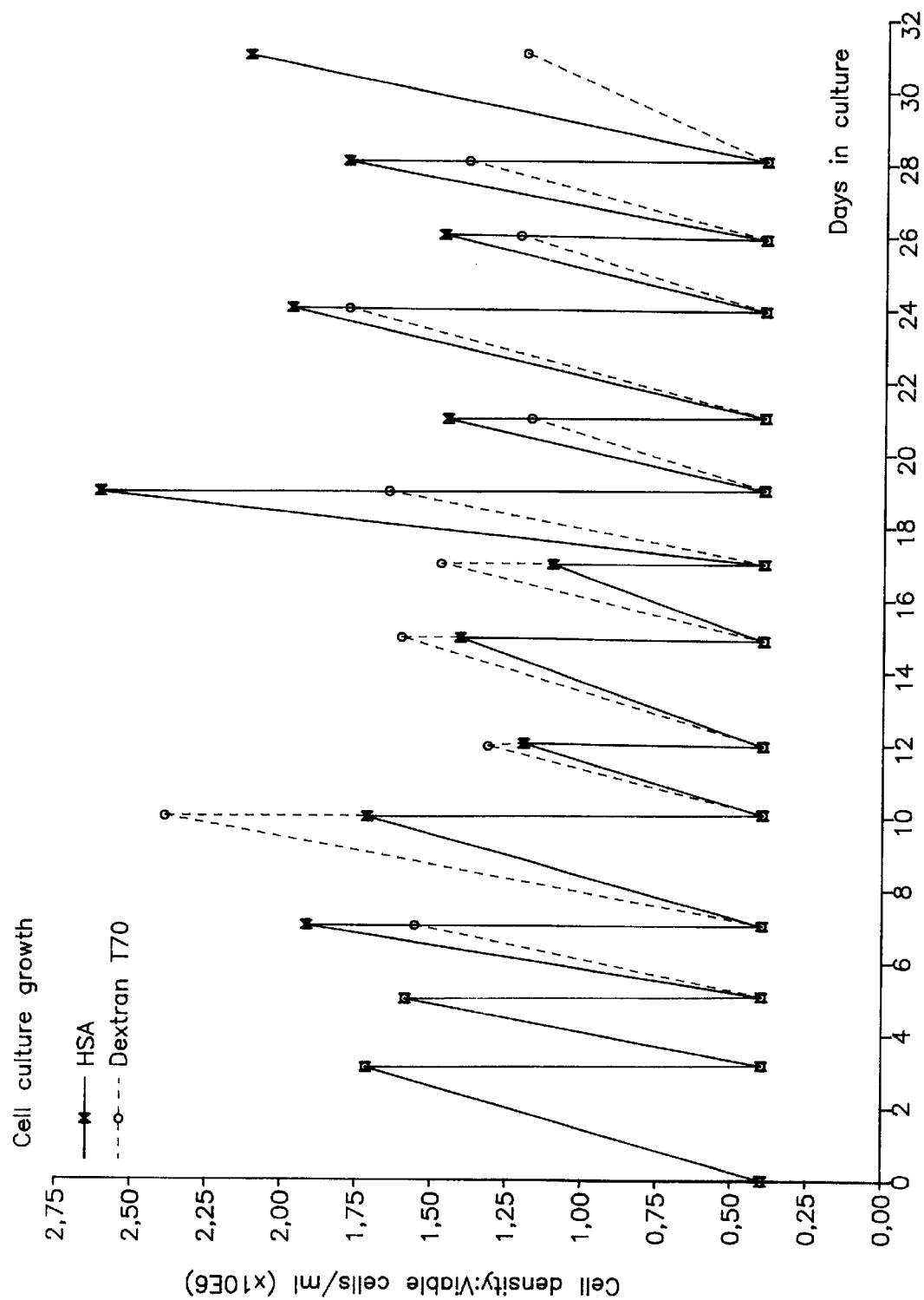
FIG. 1 is a diagram showing long-term cell culture growth (cell density vs time) for rVIII-CHO cells in serum-free medium supplemented with either HSA or dextran $M_w$ 70,000, respectively.

CHO cells were transfected with a gene capable of directing the expression of a recombinant Factor VIII, essentially produced as described in WO 91/09122 (Examples 1 to 3) and hereinafter referred to as "rVIII SQ". The cells were grown as a suspension culture in serum-free complete medium such as CHO—S—SFM (GIBCO BRL) containing HSA. Cells were seeded at 0.4 to 0.6—$10^6$ viable cells per ml (vc/ml) into serum-free medium containing HSA and incubated at 37° C. in an atmosphere of 5% carbon dioxide in air in spinner culture flasks. After 2 to 3 days the cell number increased to approximately 1.2 to $2.0 \times 10^6$ vc/ml with a viability of >90%. The cell number was then reduced to 0.4 to $0.6 \times 10^6$ vc/ml, the serum-free cell culture medium replaced, and the cell culture reincubated. Total cell number and viability was determined by Erythrocin-B dye exclusion using a hemocytometer. The cells were then resuspended and cultivated in serum-free medium in which HSA had been replaced by dextran $M_w$ 70,000 (Dextran T-70, Pharmacia Biotech AB, Sweden). The results from this experiment are shown in FIG. 1. As appears from the figure, no significant differences were seen between the cells cultivated in serum-free medium containing HSA compared to those cultivated in serum-free medium in which HSA was replaced by Dextran T-70.

EXAMPLE 2

Thawing of cells

Cryopreserved ampoules of the CHO cell line containing the gene encoding rVIII SQ (as for Example 1) were removed from storage in liquid nitrogen and thawed. Cells from one ampoule were resuspended in serum-free medium containing dextran $M_w$ 70,000 (Dextran T-70, Pharmacia Biotech AB, Sweden) in replacement for HSA. The cells were incubated at 37° C. in an atmosphere of 5% carbon dioxide in air in tissue culture flasks. The cell culture was observed for one month and no significant difference in growth characteristics or viability was noticed compared to cells resuspended in serum-free medium containing HSA.

EXAMPLE 3

Growth rate (dt)

Figure 2:
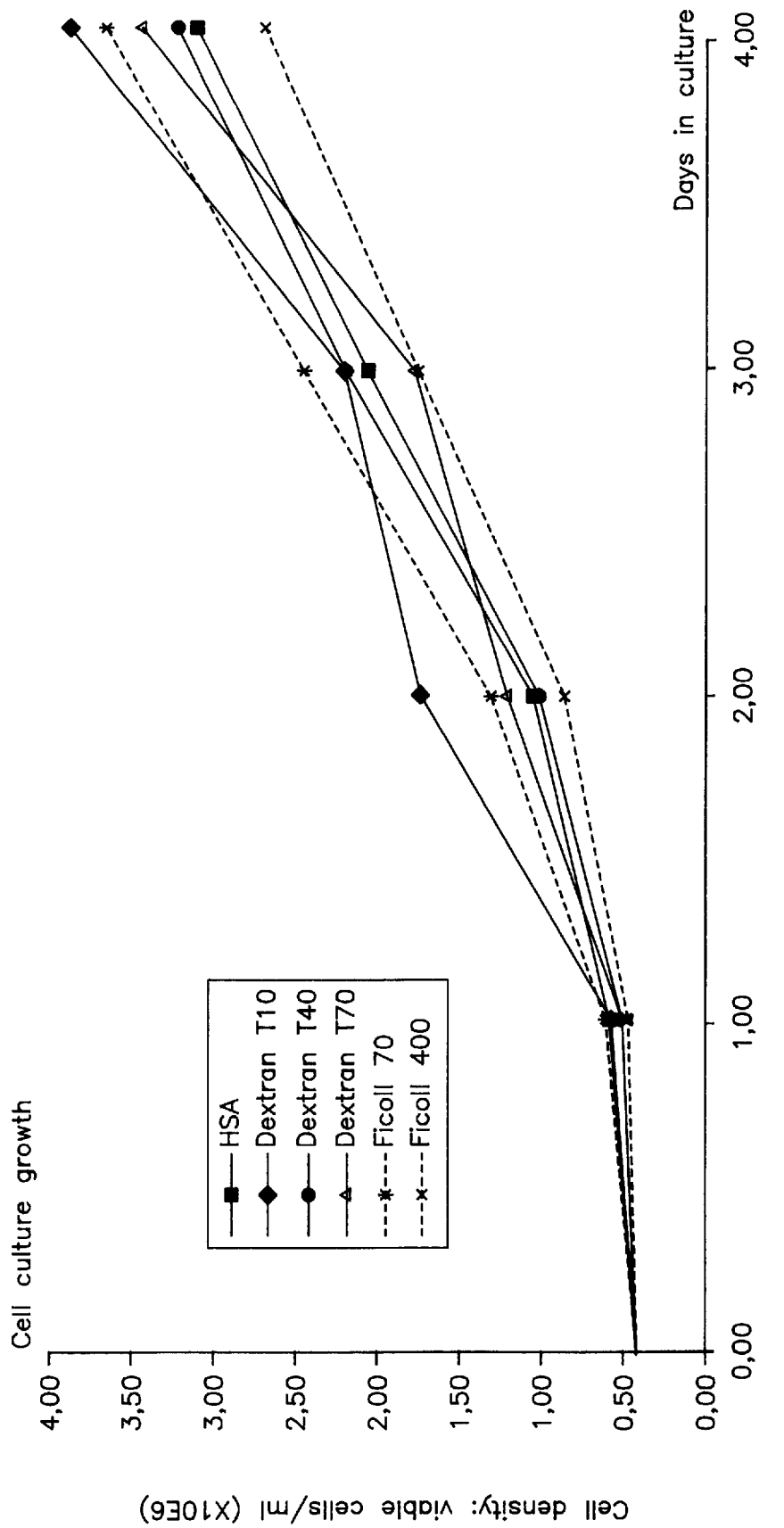
FIG. 2 is a diagram showing cell culture growth (cell density vs time) for rVIII-CHO cells in serum-free medium supplemented with one of HSA, dextran $M_w$ 10,000, dextran $M_w$ 40,000, dextran $M_w$ 70,000, Ficoll $M_w$ 70,000 and Ficoll $M_w$ 400,000.

CHO cells containing the gene encoding rVIII SQ (as for Example 1) were cultivated in serum-free medium containing HSA. Cells were then transferred into medium in which HSA was replaced by Dextran T10, Dextran T40, Dextran T70, Ficoll 70 or Ficoll 400 (all from Pharmacia Biotech AB, Sweden) at a cell density of 0.4 to 0.6×10⁶ vc/ml with a viability of >90% and incubated at 37° C. in an atmosphere of 5% carbon dioxide in air in spinner culture flasks. After 2 days the total cell number and viability were determined. The cells were then resuspended in the corresponding cell culture medium and incubated for a further 2 days, and the total cell number and viability determined daily. The population doubling time (dt) was determined for each culture. The results are shown in FIG. 2 and Table 1 below. No significant difference was seen in the growth characteristics of the cells in media containing the different supplements.

TABLE 1

| Growth rate | dt (h) |
|---|---|
| HSA | 20.7 |
| Dextran T10 (Mw 10,000) | 20.9 |
| Dextran T40 (Mw 40,000) | 23.7 |
| Dextran T70 (Mw 70,000) | 19.4 |
| Ficoll 70 (Mw 70,000) | 22.2 |
| Ficoll 400 (Mw 400,000) | 29.3 |

EXAMPLE 4

Production of rVIII

Figure 3:
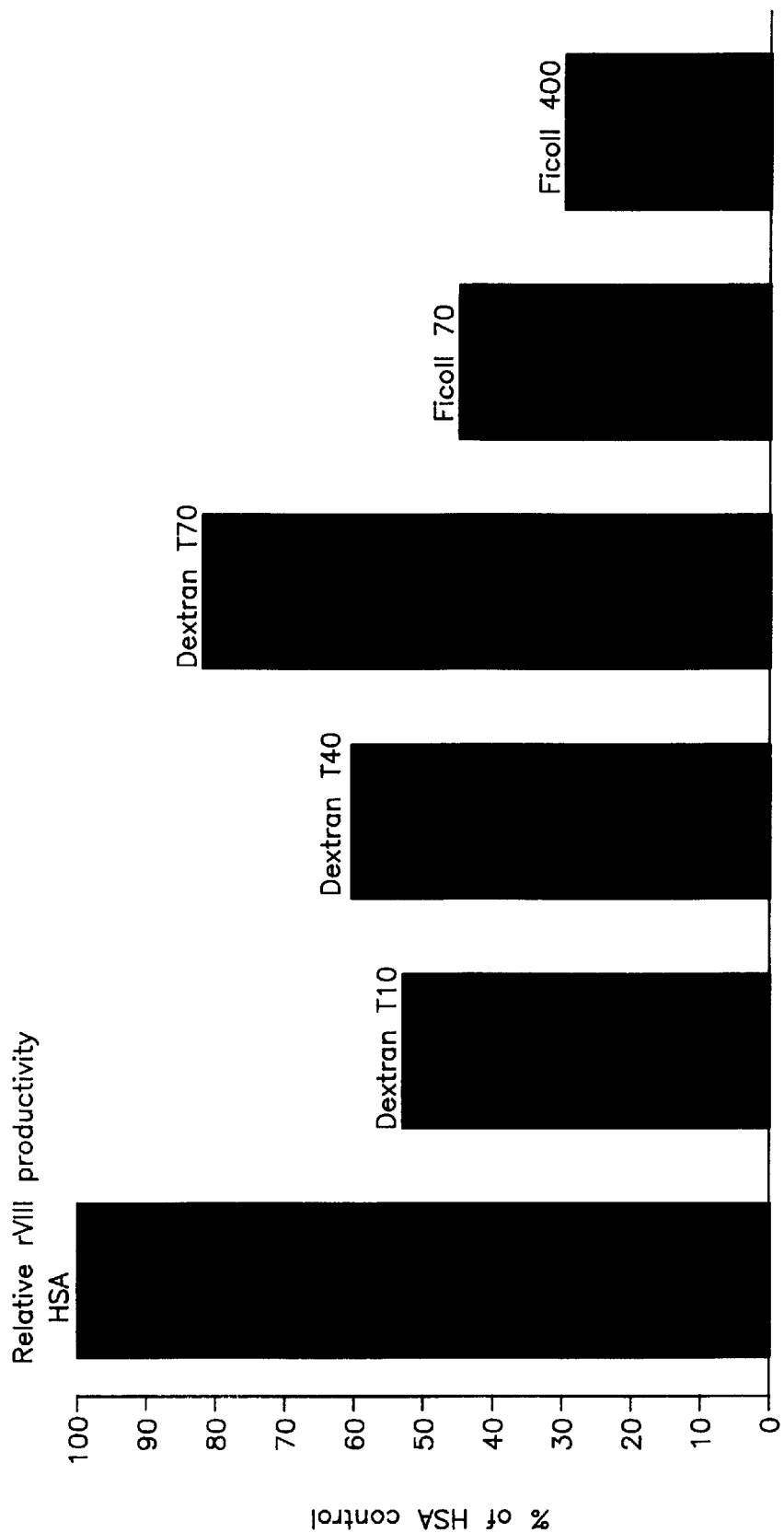
FIG. 3 is a bar chart showing the relative rVIII productivity relative to a HSA control.

CHO cells containing the gene encoding rVIII SQ (as for Example 1) were cultivated in serum-free medium containing HSA. Cells were then transferred into medium in which HSA was replaced by Dextran T10, Dextran T40, Dextran T70, Ficoll 70 or Ficoll 400 (all from Pharmacia Biotech AB, Sweden) at a cell density of 0.4 to 0.6×10⁶ vc/ml with a viability of >90% and incubated at 37° C. in an atmosphere of 5% carbon dioxide in air in spinner culture flasks. After 2 to 3 days the cell number increased to approximately 1.2 to 2.0×10⁶ vc/ml with a viability of >90%. rVIII activity for each culture was determined regularly using the Kabi Coatest Factor VIII kit (Pharmacia AB, Sweden). The results are shown in FIG. 3. rVIII was produced in each of the media containing the various polysaccharide supplements. It was found that the rVIII activity in medium containing dextran T-70 and T-40 was comparable to that found with medium containing HSA. Lower levels of rVIII were found, however, in medium supplemented with the other polysaccharide compounds.

EXAMPLE 5

Cultivation in stirred tank bioreactor

In order to show that serum-free medium in which HSA had been replaced with a polysaccharide compound was also applicable to cultivation in a stirred tank bioreactor where the cells were known to be exposed to greater shear forces the following was performed. CHO cells containing the gene encoding rVIII SQ (as for Example 1) were cultivated in serum-free medium containing Dextran T-70 in replacement for HSA in spinner flasks (as described in Example 2 above). The cells were then transferred into a 2L working volume stirred tank bioreactor (Belach AB, Sweden) at a cell density of 0.6 to 0.9×10⁶ vc/ml in 2L of fresh serum-free media containing Dextran T-70 ($M_w$ 70.000) in replacement to HSA and cultivated for 12 days. The bioreactor cultivation was compared with that in a corresponding bioreactor in which the CHO cell was cultivated in serum-free media containing HSA under the same conditions. No significant difference was seen between the growth characteristics in a stirred tank bioreactor in medium in which HSA was replaced with Dextran T-70 to that seen where the medium contained HSA, as is shown in FIG. 4. This bioreactor cultivation also confirmed that rVIII was produced.

In Examples 1 to 5 above corresponding results were obtained where Dextran T-40 and T-70, respectively, were replaced by the corresponding pharmaceutical grade products.

We claim:

1. A method of cultivating mammalian cells expressing recombinant Factor VIII in a serum-free cell culture medium that requires the presence of human serum albumin (HSA) and which is essentially free from fatty acids, fatty acid esters and lipids, which comprises replacing HSA with at least one glucose or sucrose based polysaccharide comprising dextrans, partially hydrolyzed native dextran or Ficoll, and having an average molecular weight of from about 10,000 to about 450,000, with the exception of polycationic and polyanionic glucose or sucrose based polysaccharides.

2. The method according to claim 1 wherein said polysaccharide has an average molecular weight of from about 40,000 to about 400,000.

3. The method according to claim 2, wherein said mammalian cells are CHO cells.

4. The method according to claim 2, wherein said polysaccharide has an average molecular weight of from about 40,000 or about 70,000.

5. The method according to claim 1, wherein said mammalian cells are CHO cells.

6. The method according to claim 1, wherein the cells are cultivated in a suspension cell culture.

7. The method according to claim 6, wherein the cells are cultivated in a stirred tank bioreactor.

8. The method according to claim 1 wherein recombinant Factor VIII is an active truncated derivative of recombinant Factor VIII.

9. The method according to claim 8, wherein the active truncated derivative of recombinant Factor VIII is recombinant Factor VIII SQ (rVIII SQ).

10. A method of cultivating mammalian cells expressing recombinant Factor VIII in a serum-free cell culture medium that requires the presence of human serum albumin (HSA) and which is essentially free from fatty acids, fatty acid esters and lipids, which comprises replacing HSA with at least one glucose or sucrose based polysaccharide selected from dextran and copolymers of sucrose and epichlorhydrin, having an average molecular weight of from about 10,000 to about 450,000.

11. The method according to claim 10, wherein said dextran has an average molecular weight of from about 40,000 or about 70,000.

12. The method according to claim 10, wherein said polysaccharide has an average molecular weight of from about 40,000 to about 400,000.

13. The method according to claim 10, wherein said mammalian cells are CHO cells.

* * * * *